(12) United States Patent
Sunayama

(10) Patent No.: US 6,315,749 B1
(45) Date of Patent: Nov. 13, 2001

(54) FOOT SUPPORTER

(75) Inventor: Masamitsu Sunayama, Tokyo (JP)

(73) Assignee: Tokyo Hosiery Co., Ltd., Tokyo (JP)

( * ) Notice: Subject to any disclaimer, the term of this patent is extended or adjusted under 35 U.S.C. 154(b) by 0 days.

(21) Appl. No.: 09/618,153

(22) Filed: Jul. 17, 2000

(30) Foreign Application Priority Data

Jul. 16, 1999 (JP) .................................................. 11-202985

(51) Int. Cl.[7] .................................................. A61F 5/00
(52) U.S. Cl. .............................. 602/23; 602/30; 128/882
(58) Field of Search .................................. 602/23, 30, 31, 602/60, 61, 62, 66; 128/846, 882, 892, 893

(56) References Cited

U.S. PATENT DOCUMENTS

| | | | |
|---|---|---|---|
| 1,784,032 | * 12/1930 | Stern | 602/30 |
| 3,303,842 | * 2/1967 | Horlacher | 602/30 |
| 4,940,046 | * 7/1990 | Jacoby | 602/30 |
| 5,267,945 | * 12/1993 | Doctor | 602/30 |
| 6,093,163 | * 7/2000 | Chong | 602/30 |

FOREIGN PATENT DOCUMENTS

| | | |
|---|---|---|
| 63-212354 | 9/1988 | (JP) . |
| 6-7714 | 3/1994 | (JP) . |
| 6-7715 | 3/1994 | (JP) . |
| 6-13814 | 4/1994 | (JP) . |
| 6-13815 | 4/1994 | (JP) . |

* cited by examiner

*Primary Examiner*—Michael A. Brown
(74) *Attorney, Agent, or Firm*—Sughrue, Mion, Zinn, Macpeak & Seas, PLLC

(57) ABSTRACT

A foot supporter includes a tubular body and a first-toe receiving portion. The tubular body is formed of knit fabric and is stretchable in the transverse direction of the foot. The tubular body is adapted to receive the tread portion of the foot and compress root portions of metatarsal bones in the tread portion. The first-toe receiving portion is formed of knit fabric and is stretchable in the longitudinal direction of the foot. The first-toe receiving portion is attached to the front end of the tubular body end to be located on the inner side of the foot. The first-toe receiving portion includes a sack portion at the tip end thereof and an opening at the base end thereof such that the opening is opened toward the second toe.

3 Claims, 9 Drawing Sheets

FOOT SUPPORTER

BACKGROUND OF THE INVENTION

1. Field of the Invention

The present invention relates to a foot supporter formed of knit fabric, and more particularly to a foot supporter which is fitted on a foot in order to restore distorted arches on the sole of the foot to their original shapes to thereby recover the normal functions of the foot, as well as to correction of deformation of the first toe (hallux, the big toe) such as hallux valgus.

2. Description of the Related Art

Figures 10A, 10B:
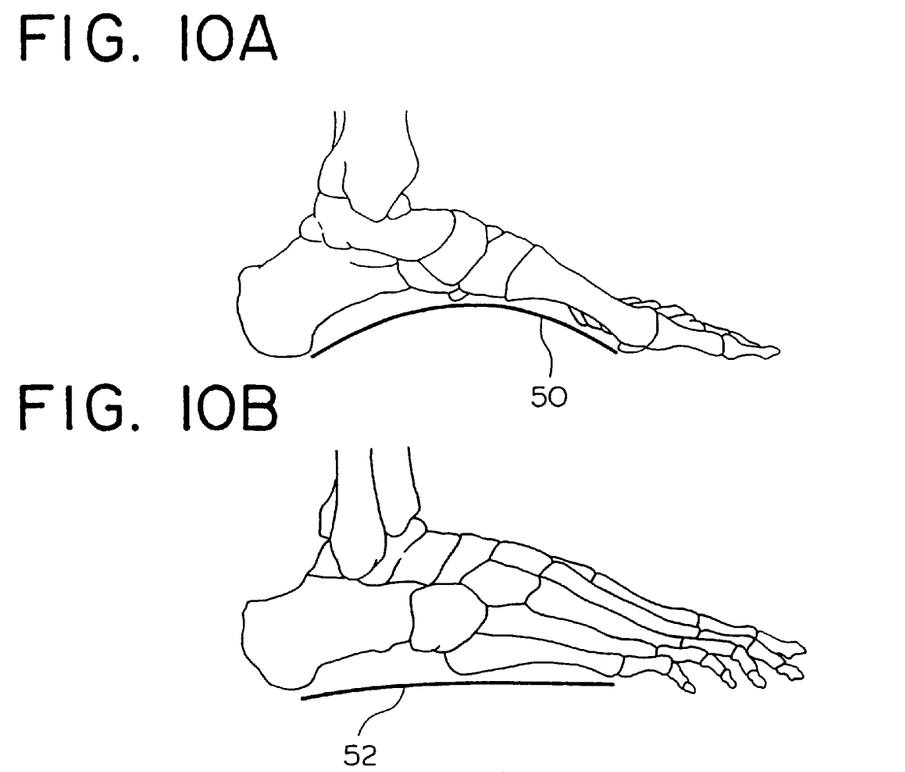
FIG. 10 is an explanatory view showing arches on the sole of the foot.
Figure 10C:
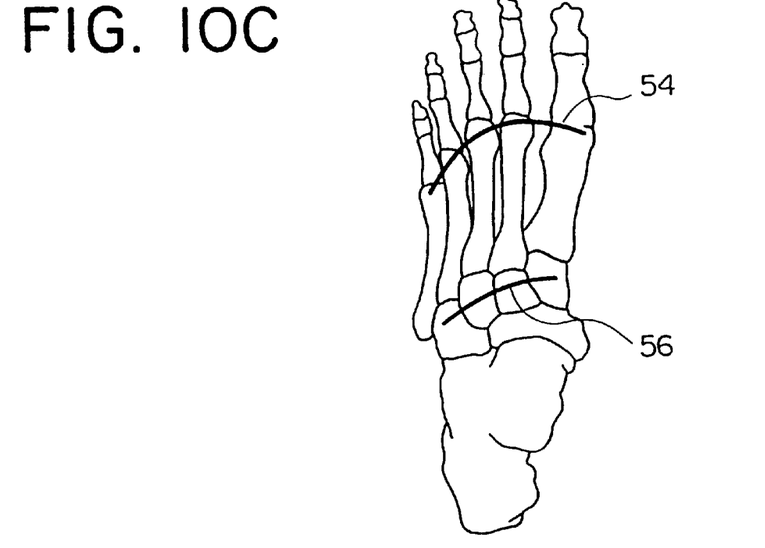

Recently, due to changes in lifestyles and cultures, an increasing number of persons have suffered foot problems such as distortion of arches on the sole of the foot and hallux valgus. As shown in FIGS. 10A, 10B, and 10C, arches on the sole of the foot include a longitudinal arch 50 on the inner side of the foot, a longitudinal arch 52 on the outer side of the foot, a metatarsal arch 54 on the front side of the foot, and a lateral arch 56 on the root side of the foot. These arches on the sole of the foot are necessary for proper functioning of the foot. Therefore, a person having a distorted arch on the sole of his foot may find difficulty in walking, running, or exercising.

Figure 11:
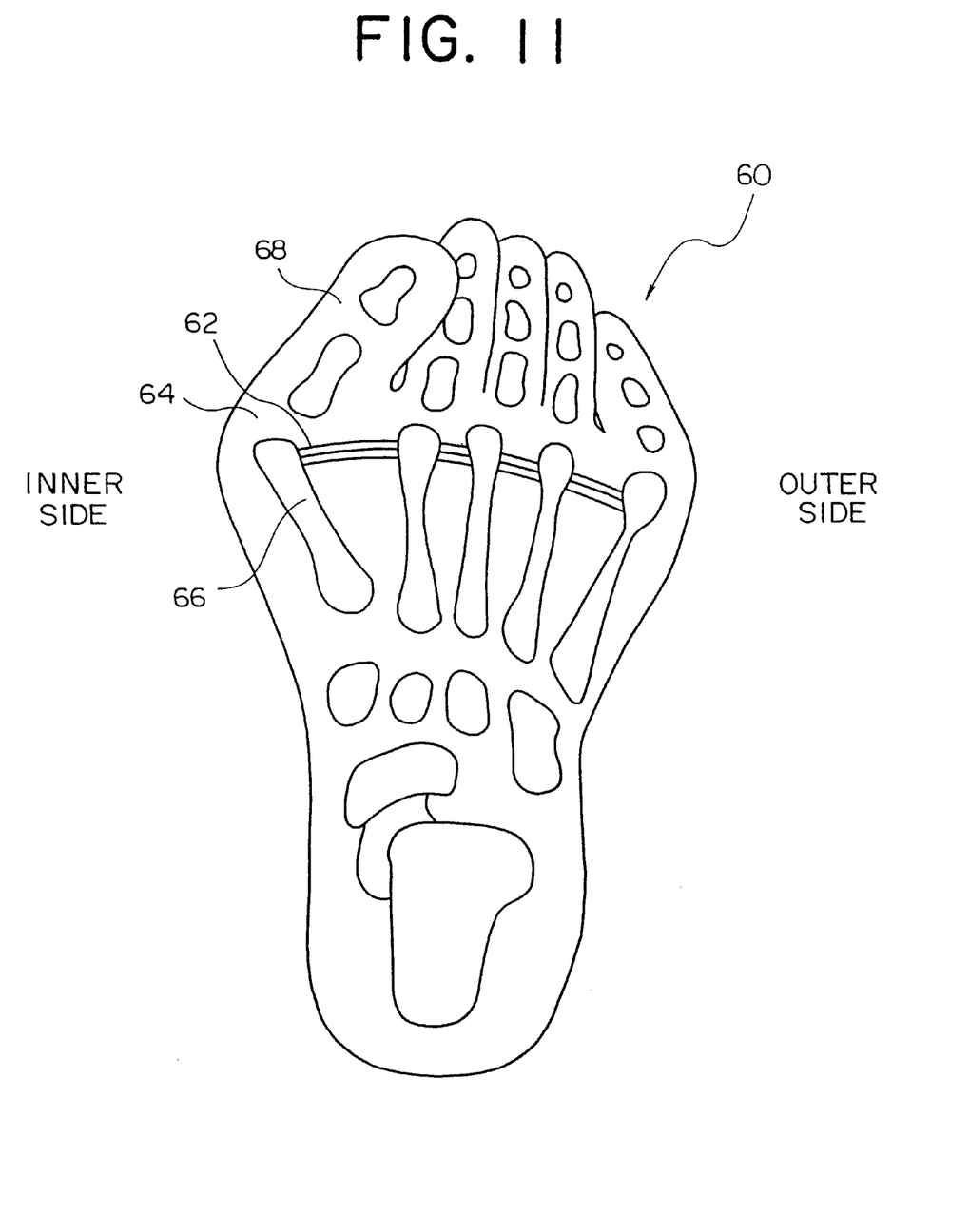
FIG. 11 is an explanatory view showing hallux valgus.

Hallux valgus is a type of deformation of the foot. As shown in FIG. 11, the lateral metatarsal ligament 62 is loosened and metatarsal joints 64 spread, thereby causing varus (deformation toward the inner side of the foot) of the first metatarsal bone 66, resulting in valgus (deformation toward the outer side of the foot) of the first toe 68.

Conventionally, various kinds of foot supporters have been proposed for correcting the above-mentioned hallux valgus. For example, supporters for correcting hallux valgus are disclosed in JP-B-1990-12094, JU-A-1994-7714, JU-A-1994-7715, JU-A-1994-13814 and JU-A-1994-13815. The basic function of these supporters for correction of hallux valgus is to return spread metatarsal joints and metatarsal bones to their original positions and fix them in place and to bring the first toe back to the proper orientation, so that hallux valgus is corrected.

However, there has not been proposed a foot supporter which is fitted on the foot in order to restore distorted arches on the sole of the foot to their original shapes.

As described above, various kinds of conventional supporters for correction of hallux valgus have been proposed. These supporters are formed of relatively thick and strong fabric which is substantially non-stretchable. Therefore, the conventional supporter for correction of hallux valgus provides an unfavorable sensation upon being placed on the foot, and makes it difficult to wear a sock or a shoe over the supporter.

SUMMARY OF THE INVENTION

An object of the present invention is to solve the above-mentioned problems, and to provide a foot supporter which enables recovery of a distorted arch on the sole of the foot so as to recover the proper function of the foot, as well as correction of deformation of the first toe such as hallux valgus, which can be comfortably fitted on the foot, and over which a sock or a shoe can be put on smoothly.

To achieve the above object, the present invention provides a foot supporter comprising a tubular body and a first-toe receiving portion. The tubular body is formed of knit fabric and is stretchable in the transverse direction of the foot. The tubular body is adapted to receive the tread portion of the foot and compress root portions of metatarsal bones in the tread portion. The first-toe receiving portion is formed of knit fabric and is stretchable in the longitudinal direction of the foot. The first-toe receiving portion is attached to the front end of the tubular body end to be located on the inner side of the foot. The first-toe receiving portion includes a sack portion at the tip end thereof and an opening at the base end thereof such that the opening is opened toward the second toe.

When a user wears the foot supporter according to the present invention, the user inserts the tread portion of the foot into the tubular body, such that the first toe is inserted into the sack portion of the first-toe receiving portion, and the second to the fifth toe are projected from the front opening of the tubular body. Thus, the foot supporter compresses the root portions of the metatarsal bones in the tread portion of the foot by means of forces in directions toward the widthwise center of the foot to thereby assist the function of the lateral metatarsal ligament and to thereby restore the shapes of flattened arches on the sole of the foot in order to recover the proper functions of the foot.

Further, since the tubular body compresses the root portions of the metatarsal bones in the tread portion of the foot, spread metatarsal joints and metatarsal bones can be brought back to their original positions and fixed in place. In addition, the first-toe receiving portion produces a contraction force in the longitudinal direction in order to pull the first toe towards the inner side of the foot to thereby return the bent first toe to its normal posture and fix it in place. In other words, since the opening is formed at the base portion of the first-toe receiving portion to face the second toe, the contraction force that the first-toe receiving portion produces in the longitudinal direction of the foot produces a component force for pulling the first toe towards the inner side of the foot. Thus, the foot supporter according to the present invention corrects hallux valgus.

In the foot supporter according to the present invention, since the tubular body compresses the root portions of the metatarsal bones in the tread portion of the foot, the foot supporter can restore distorted arches on the foot sole and correct hallux valgus without providing pain to the user. That is, in the above-described conventional supporter for correction of hallux valgus is designed to compress portions of the metatarsal bones located on the front side with respect to their root portions. In this case, the user may feel pain. By contrast, the foot supporter of the present invention does not have such a drawback.

Moreover, in the foot supporter of the present invention, since the tubular body and the first-toe receiving portion are formed separately, and connected with each other, the position of the tubular body on the tread portion of the foot can be changed with ease. Therefore, through a change in the position of the tubular body on the tread portion of the foot, the force that pulls the first toe towards the inner side of the foot can be adjusted in order to cope with various symptoms caused by deformation of the foot.

Although no specific limitation is imposed on the structure of the foot supporter according to the present invention, the following structures (1) and (2) are preferred.

(1) The first-toe receiving portion is formed from two leaf-shaped pieces of fabric, which are sewn together along their edges in an inner-side region extending from a base end to a tip end corner on the second-toe side. The base portions of the two pieces of fabric are sewn to the tubular body such that the first-toe receiving portion is attached to the front end of the tubular body to be located at the widthwise inner end of the tubular body.

(2) The first-toe receiving portion is formed from two substantially rectangular pieces of fabric, which are sewn together at their tip end portions. The base end portion of one piece of fabric is sewn to the tubular body with the piece of fabric being twisted 360°, and the base end portion of the other piece of fabric is sewn to the tubular body without the piece of fabric being twisted. Thus, the first-toe receiving portion is attached to the front end of the tubular body to be located at the widthwise inner end thereof.

In the present invention, the compression force (pressure) that the tubular body applies to the root portions of the metatarsal bones in the tread portion of the foot is preferably 24 mh or greater, more preferably from 24 to 34 mh, in order to improve effectiveness in restoring arches on the sole of the foot and correcting hallux valgus.

In addition, in the present invention, the knit fabric used for forming the tubular body and the first-toe receiving portion preferably has a thickness of 0.8 mm or less, more preferably 0.3 to 0.8 mm, as measured in a fitted state, in consideration of sensation upon being placed on the foot, and easiness in wearing a sock or a shoe over the supporter. For example, knit fabric of polyurethane fiber having a thickness above 400 denier is used.

DESCRIPTION OF THE PREFERRED EMBODIMENTS

Embodiments of the present invention will next be described in detail with reference to the drawings; however, the present invention is not limited to the embodiments.

First Embodiment

Figure 1:
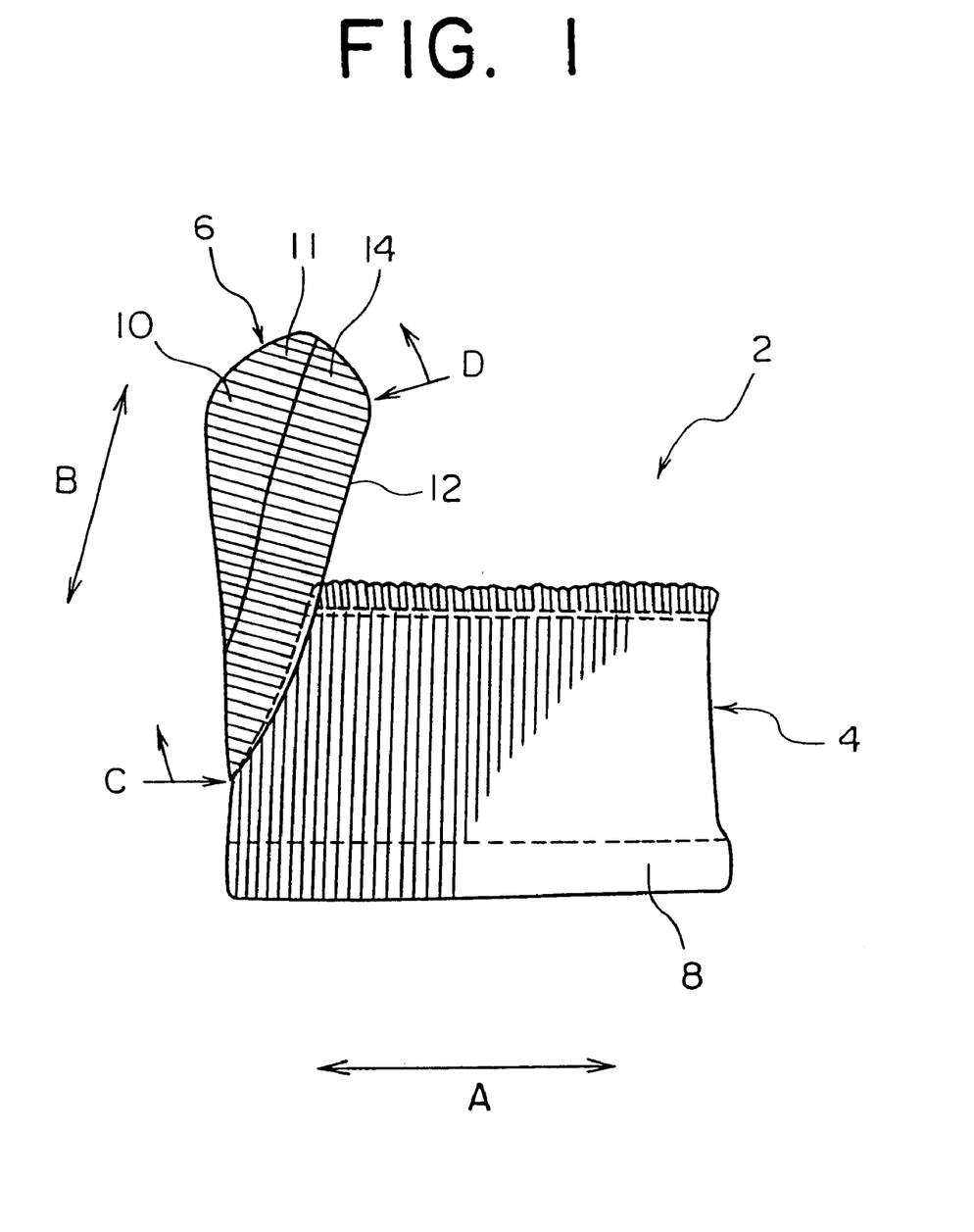
FIG. 1 is a front view showing a foot supporter according to a first embodiment of the present invention.
Figure 2:
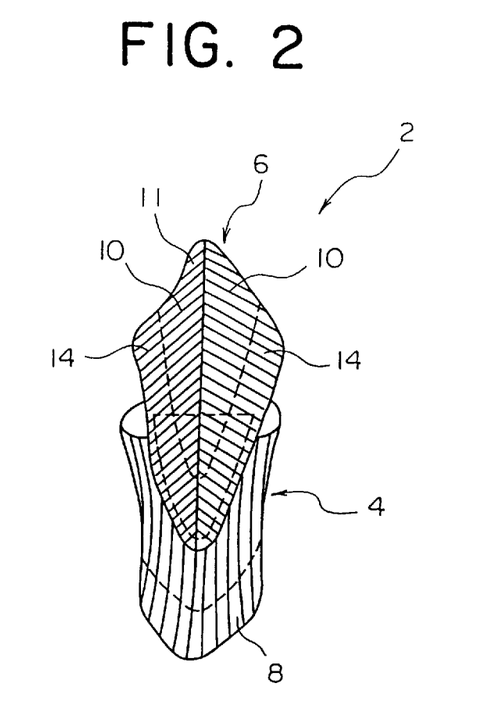
FIG. 2 is a left side view of the supporter shown in FIG. 1.
Figure 3:
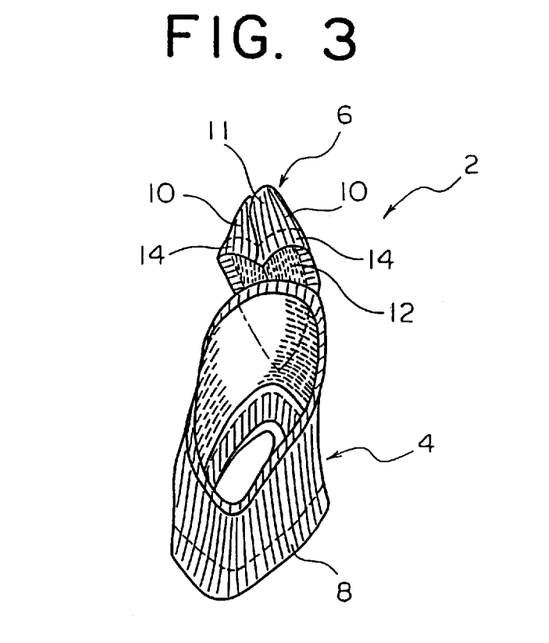
FIG. 3 is a right side view of the supporter shown in FIG. 1.

FIGS. 1 to 3 show a foot supporter according to a first embodiment of the present invention. FIG. 1 is a front view, FIG. 2 is a left side view, and FIG. 3 is a right side view. The foot supporter 2 of the present embodiment comprises a tubular body 4 and a first-toe receiving portion 6. The tubular body 4 is formed of knit fabric and is stretchable in the transverse direction A of the foot. The first-toe receiving portion 6 is formed of knit fabric and is stretchable in the longitudinal direction B of the foot (actually, in a direction slightly inclined with respect to the longitudinal direction). The tubular body 4 is stretchable also in the longitudinal direction of the foot, and the first-toe receiving portion 6 in the transverse direction of the foot.

The tubular body 4 is knitted cylindrically, and a lower end portion 8 thereof in FIG. 1 is folded and tucked up, so that the fabric is doubled at the lower end portion 8. Therefore, when the tread portion of the foot is inserted into the tubular body 4, the root portions of the metatarsal bones in the tread portion are compressed by the end portion 8.

The first-toe receiving portion 6 is formed from two leaf-shaped pieces of fabric 10. The pieces of fabric 10 are sewn together along their edges in an inner-side region extending from a lower end (denoted by C in FIG. 1) to an upper corner (denoted by D in FIG. 1) on the second-toe side. Thus, the first-toe receiving portion 6 has a sack portion 11 at the tip end portion and an opening 12 at the base portion thereof such that the opening 12 opens toward the second-toe side. The lower portions of the two pieces of fabric 10 are sewn to the tubular body 4 such that first-toe receiving portion 6 is attached to the front end of the tubular body 4 to be located at the widthwise inner end thereof. Edge portions 14 of the pieces of fabric 10 located on the second-toe side are folded and tucked up so as to be doubled.

Figure 4:
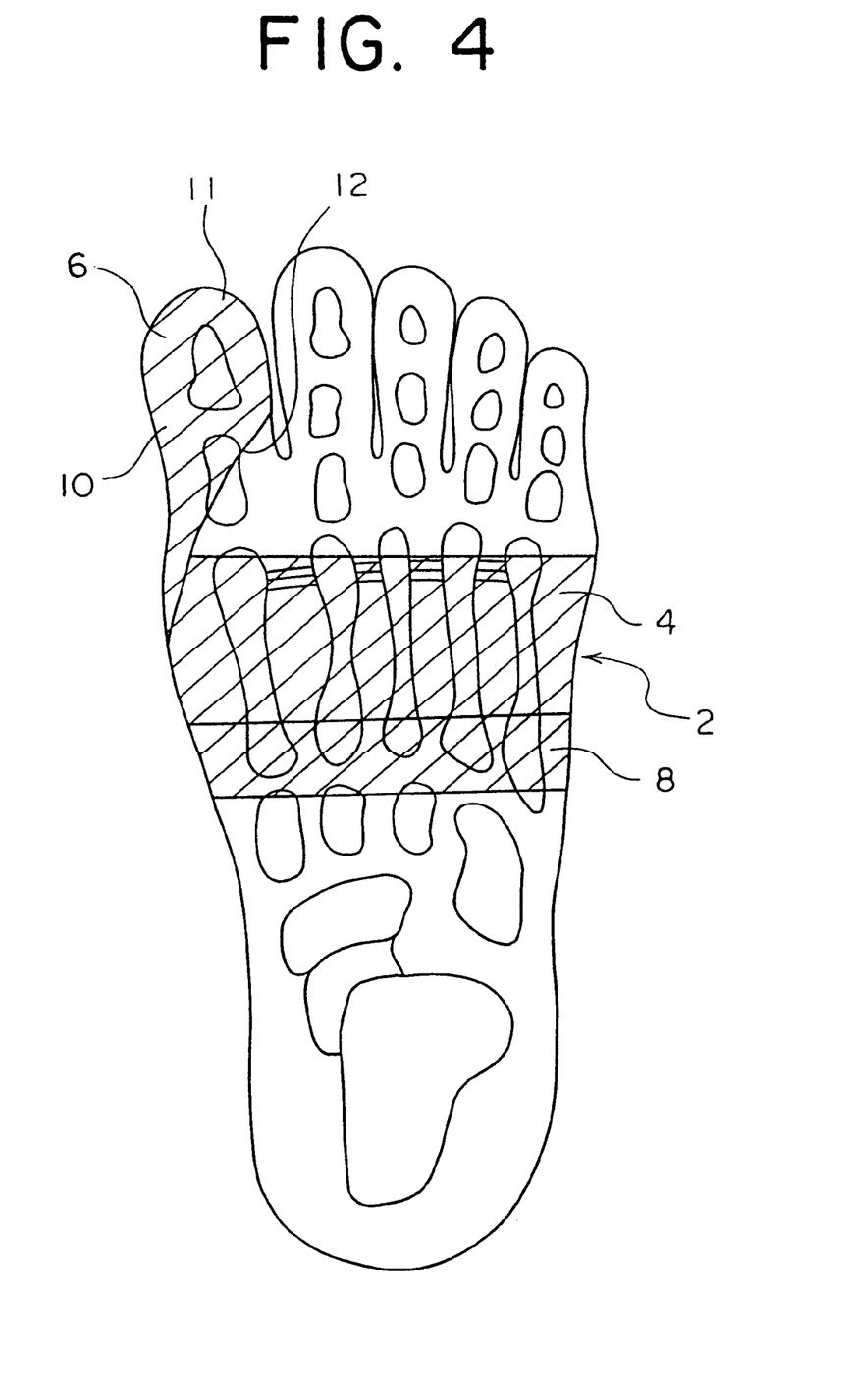
FIG. 4 is an explanatory view showing a state in which the foot supporter according to the first embodiment is placed on the foot.

A method of using the foot supporter 2 according to the present embodiment will now be described. During fitting of the foot supporter according to the present embodiment, as shown in FIG. 4, the tread portion of the foot is inserted into the tubular body 4, such that the first toe is inserted into the sack portion 11 of the first-toe receiving portion 6, and the second to fifth toes are projected out of the front opening of the tubular body 4. Thus are obtained the effects (1) and (2) described below, so that the distorted arches on the foot sole are restored to their original shapes, and hallux valgus is corrected.

Figure 5:
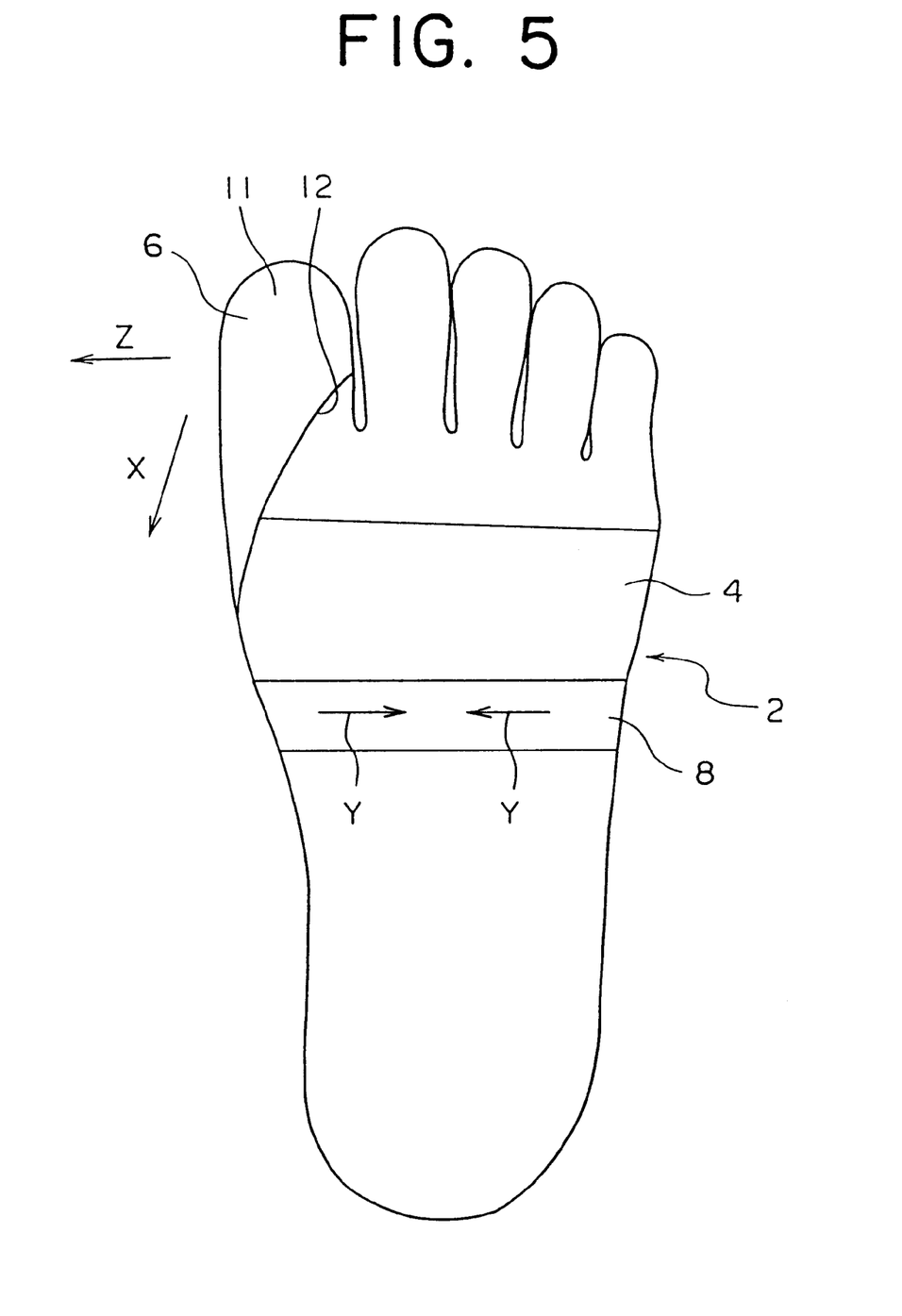
FIG. 5 is another explanatory view showing a state in which the foot supporter according to the first embodiment is placed on the foot.

(1) As shown in FIG. 5, the end portion 8 of the tubular body 4 where fabric is doubled produces a force in directions y toward the widthwise center of the foot, thereby compressing the root portions of the metatarsal bones in the tread portion of the foot. Thus, the distorted arches on the sole of the foot (particularly the lateral arch at the root portion of the foot) are restored to their original shapes to thereby recover the proper functions of the foot.

(2) As mentioned above, the end portion 8 of the tubular body 4 where fabric is doubled compresses the root portions of the metatarsal bones in the tread portion of the foot. Therefore, the spread metatarsal joints and the metatarsal bones can be brought back to their original positions and fixed in place. In addition, the first-toe receiving portion 6 produces a contraction force in the longitudinal direction x in order to pull the first toe towards the inner side of the foot to thereby return the bent first toe to its normal orientation and fix it in place. In other words, since the opening 12 is formed at the lower portion of the first-toe receiving portion 6 to face the second toe, the contraction force that the first-toe receiving portion 6 produces in the longitudinal direction x of the foot produces a component force for pulling the first toe in the direction of arrow z (towards the inner side of the foot). Thus, correction of hallux valgus is effected.

Second Embodiment

Figure 6:
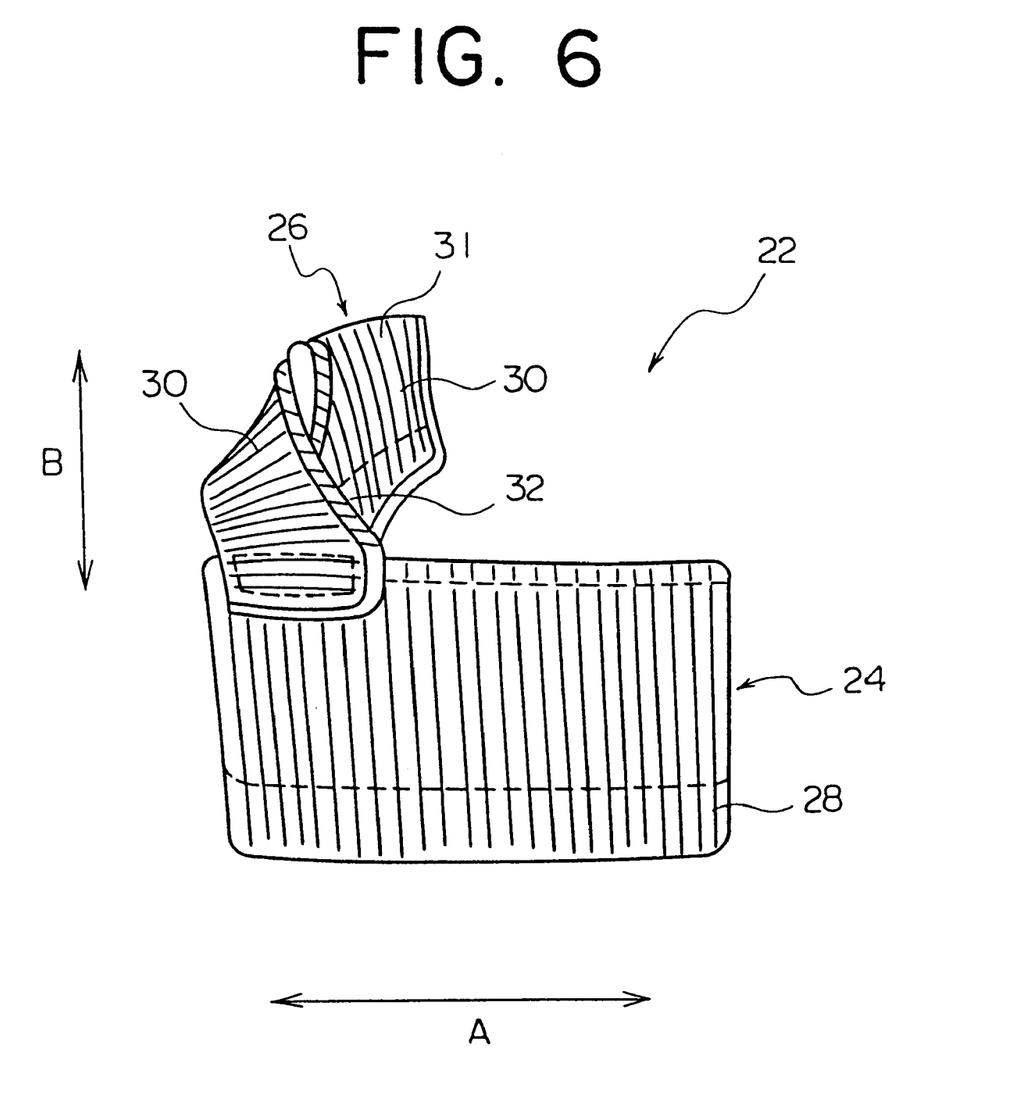
FIG. 6 is a front view showing a foot supporter according to a second embodiment of the present invention.
Figure 7:
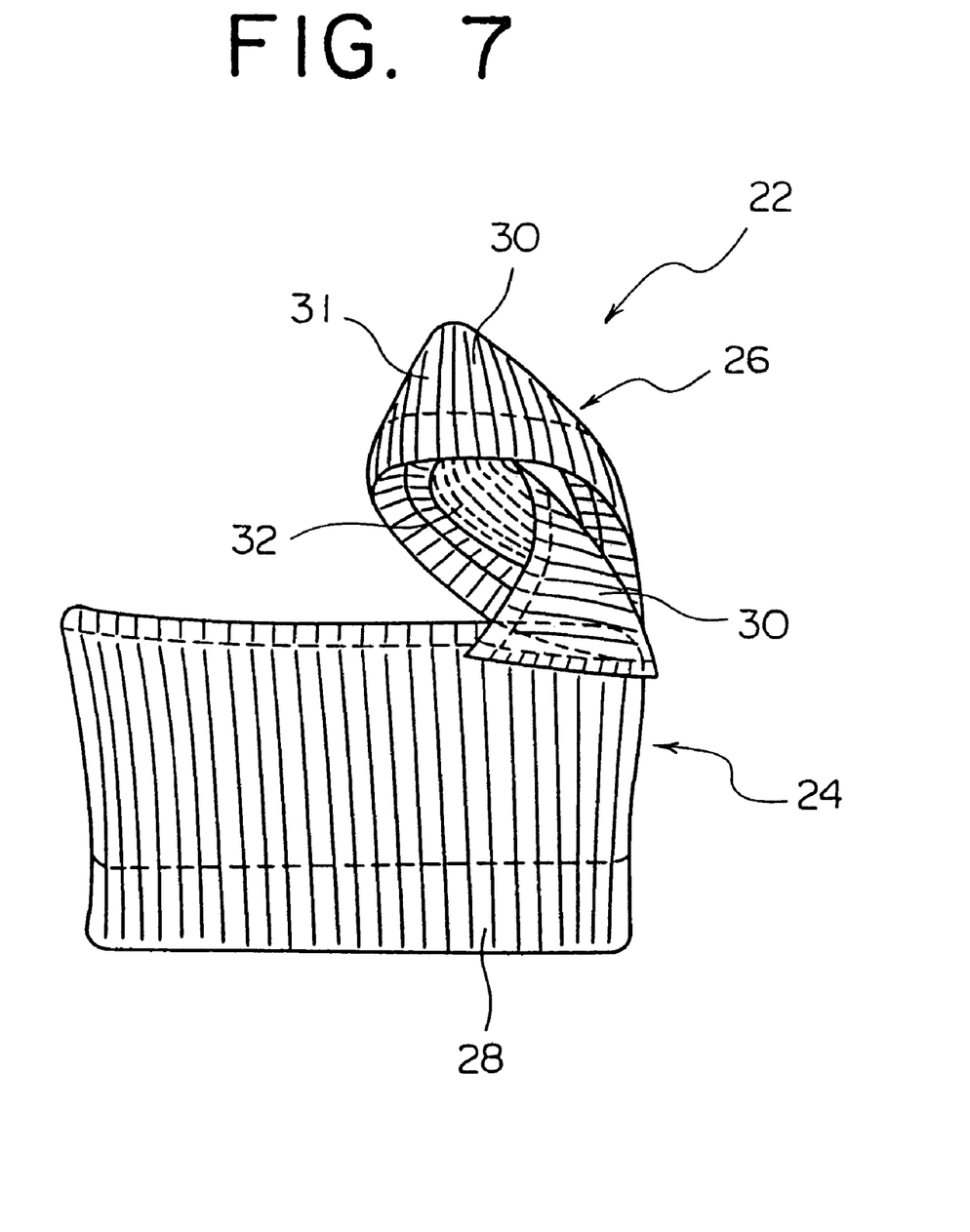
FIG. 7 is a rear view of the supporter shown in FIG. 6.
Figure 8:
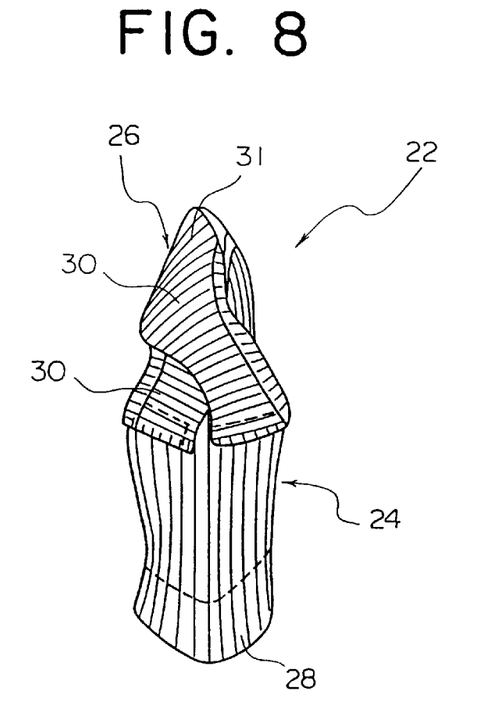
FIG. 8 is a left side view of the supporter shown in FIG. 6.
Figure 9:
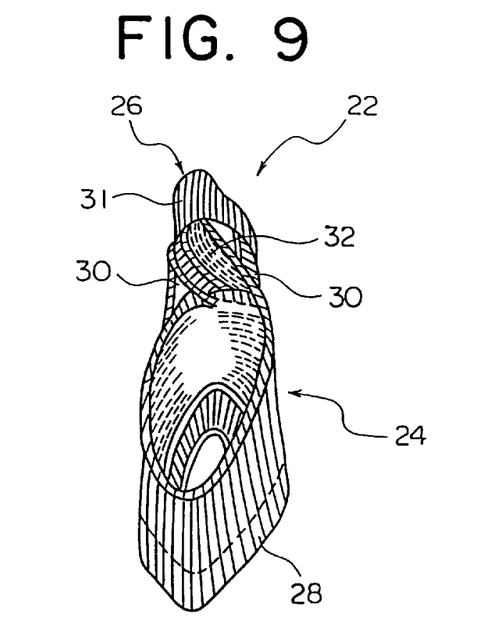
FIG. 9 is a right side view of the supporter shown in FIG. 6.

FIGS. 6 to 9 show a foot supporter according to a second embodiment of the present invention. FIG. 6 is a front view, FIG. 7 is a rear view, FIG. 8 is a left side view, and FIG. 9 is a right side view. The foot supporter 22 of the present embodiment comprises a tubular body 24 and a first-toe receiving portion 26. The tubular body 24 is formed of knit fabric and is stretchable in the transverse direction A of the foot. The first-toe receiving portion 26 is formed of knit fabric and is elastic in the longitudinal direction B of the foot. The tubular body 24 is stretchable also in the longitudinal direction of a foot, and the first-toe receiving portion 26 in the transverse direction of the foot.

The tubular body 24 is knitted cylindrically, and a lower end portion 28 of the tubular body 24 is folded and tucked up so that the fabric is doubled at the lower end portion 28. When the tread portion of the foot is inserted into the tubular body 24, the root portions of the metatarsal bones in the tread portion are compressed by the lower end portion 28.

The first-toe receiving portion 26 is formed of two substantially rectangular pieces of fabric 30, which are sewn together at the tip end portions.

Thus, the first-toe receiving portion 26 has a sack portion 31 at the tip end portion and an opening 32 at the base portion thereof such that the opening 32 opens toward the second-toe side. The first-toe receiving portion 26 is attached to the front end of the tubular body 24 to be located at the widthwise inner end thereof, in the following manner. The lower end portion of one piece of fabric 30 is sewn to the tubular body 24 with the piece of fabric 30 being twisted 360°, and the lower end portion of the other piece of fabric 30 is sewn to the tubular body 24 without the piece of fabric 30 being twisted.

A method of using the foot supporter 22 according to the present embodiment will now be described. During fitting of the foot supporter according to the present embodiment, the tread portion of the foot is inserted into the tubular body 24, such that the first toe is inserted into the sack portion 31 of the first-toe receiving portion 26, and the second to fifth toes are projected out of the front opening of the tubular body 24. Thus are obtained the above-described effects (1) and (2), so that the arches on the sole of the foot are restored to their original shapes, and hallux valgus is corrected. Since the state of attachment of the foot supporter of the present embodiment is substantially the same as that shown in FIG. 4, the state of attachment of the foot supporter of the present embodiment is not illustrated.

As described above, the foot supporter according to the present invention can restore distorted arches on the sole of the foot so as to recover the proper functions of the foot and also corrects deformation of the first toe such as hallux valgus. Moreover, the foot supporter according to the present invention provides a favorable sensation to a user upon being placed on the foot, and the user can wear easily a sock or a shoe over the foot supporter. The foot supporter can restore distorted arches on the sole of the foot and correct hallux valgus without providing pain to the user. Moreover, through a change in the position of the tubular body on the tread portion of the foot, the force that pulls the first toe towards the inner side of the foot can be adjusted in order to cope with various symptoms caused by deformation of the foot.

What is claimed is:

1. A foot supporter comprising:

a tubular body formed of knit fabric and stretchable in the transverse direction of a foot, the tubular body being adapted to receive a tread portion of the foot and compress root portions of metatarsal bones in the tread portion; and a first-toe receiving portion formed of knit fabric and stretchable in the longitudinal direction of the foot, the first-toe receiving portion being attached to a front end of the tubular body end to be located on the inner side of the foot and including a sack portion at a tip end and an opening at a base end such that the opening is opened toward the second toe.

2. A foot supporter according to claim 1, wherein the first-toe receiving portion is formed from two leaf-shaped pieces of fabric, which are sewn together along their edges in an inner-side region extending from a base end to a tip end corner on the second-toe side; and base portions of the two pieces of fabric are sewn to the tubular body such that the first-toe receiving portion is attached to the front end of the tubular body to be located at the widthwise inner end of the tubular body.

3. A foot supporter according to claim 1, wherein the first-toe receiving portion is formed from two substantially rectangular pieces of fabric, which are sewn together at their tip end portions; and a base end portion of one piece of fabric is sewn to the tubular body with the piece of fabric being twisted 360°; and a base end portion of the other piece of fabric is sewn to the tubular body without the piece of fabric being twisted, so that the first-toe receiving portion is attached to the front end of the tubular body to be located at the widthwise inner end thereof.

\* \* \* \* \*